(12) United States Patent
Collings et al.

(10) Patent No.: US 9,113,937 B2
(45) Date of Patent: *Aug. 25, 2015

(54) SURGICAL FORCEPS

(71) Applicant: COVIDIEN LP, Mansfield, MA (US)

(72) Inventors: Chase Collings, Hayden, ID (US);
Grant T. Sims, Littleton, CO (US);
Jeffrey R. Townsend, Loveland, CO (US)

(73) Assignee: Covidien LP, Mansfield, MA (US)

(*) Notice: Subject to any disclaimer, the term of this patent is extended or adjusted under 35 U.S.C. 154(b) by 52 days.

This patent is subject to a terminal disclaimer.

(21) Appl. No.: 14/153,346

(22) Filed: Jan. 13, 2014

(65) Prior Publication Data
US 2014/0128867 A1 May 8, 2014

Related U.S. Application Data

(63) Continuation of application No. 13/180,018, filed on Jul. 11, 2011, now Pat. No. 8,628,557.

(51) Int. Cl.
| | |
|---|---|
| *A61B 17/00* | (2006.01) |
| *A61B 17/285* | (2006.01) |
| *A61B 18/14* | (2006.01) |
| *A61B 18/08* | (2006.01) |
| *A61B 17/28* | (2006.01) |
| *A61B 18/00* | (2006.01) |

(52) U.S. Cl.
CPC ............ *A61B 17/285* (2013.01); *A61B 18/085* (2013.01); *A61B 18/1442* (2013.01); *A61B 2017/2825* (2013.01); *A61B 2018/0063* (2013.01); *A61B 2018/1452* (2013.01); *Y10T 29/49826* (2015.01)

(58) Field of Classification Search
None
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Int'l Search Report EP 11 168458.5 dated Jul. 29, 2011.
(Continued)

*Primary Examiner* — Dianne Dornbusch
*Assistant Examiner* — Robert Lynch

(57) ABSTRACT

A forceps includes a pair of shafts each having a jaw member disposed at a distal end thereof. One (or both) of the shafts is moveable relative to the other about a pivot pin between a spaced-apart position and an approximated position to move the jaw members between an open position and a closed position. A knife assembly includes a knife blade mechanically keyed to the pivot pin and moveable between an initial position, wherein the knife blade is disposed within one of the jaw members, and an extended position, wherein the knife blade extends between the jaw members. An actuator arm(s) is mechanically keyed to the pivot pin and extends therefrom. The actuator arm(s) is moveable between an un-actuated position and an actuated position to rotate the pivot pin relative to the jaw members to move the knife blade between the initial position and the extended position.

11 Claims, 9 Drawing Sheets

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,219,354 A | 6/1993 | Choudhury et al. |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H1904 H | 10/2000 | Yates et al. |
| 6,174,309 B1 | 1/2001 | Wrublewski et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,632,269 B2 | 12/2009 | Truckai et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,628,557 B2 | 1/2014 | Collings et al. |
| 2002/0058965 A1 | 5/2002 | Andrews |
| 2002/0111624 A1 | 8/2002 | Witt et al. |
| 2006/0079891 A1 | 4/2006 | Arts et al. |
| 2007/0088356 A1 | 4/2007 | Moses et al. |
| 2009/0112246 A1 | 4/2009 | Weisshaupt et al. |
| 2011/0004208 A1 | 1/2011 | Truckai et al. |
| 2011/0054468 A1 | 3/2011 | Dycus |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 202007005510 U1 | 6/2007 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001128990 A | 5/2001 |
| JP | 2001-190564 A | 7/2001 |
| JP | 20013400 | 11/2001 |
| JP | 2002-528166 A | 9/2002 |
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 95-22943 A1 | 8/1995 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 2005/110264 A2 | 11/2005 |

OTHER PUBLICATIONS

Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.

(56) References Cited

OTHER PUBLICATIONS

Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report from corresponding application PCT/US2012/046083 mailed Jan. 31, 2013.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Supplemental European Search Report from corresponding application EP 12810946 dated Dec. 17, 2014.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.

(56) References Cited

OTHER PUBLICATIONS

Int'l Search Report EP 05020665.5 dated Feb. 27, 2006.
In'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report Ep 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.

(56) References Cited

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Graig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,799, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
Chinese Office Action from Application No. 201280034716.2 dated Jun. 3, 2015.

SURGICAL FORCEPS

CROSS-REFERENCE TO RELATED APPLICATIONS

This application is a continuation application of U.S. patent application Ser. No. 13/180,018, filed on Jul. 11, 2011, the entire contents of which are hereby incorporated herein by reference.

BACKGROUND

The present disclosure relates to a surgical forceps and, more particularly, to a surgical forceps including replaceable jaw members.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both disposable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments are cost-effective, it is important that these instruments be capable of performing the same functions as their disposable counterparts and that any disposable components of these instruments be efficiently removable and replaceable with new components.

SUMMARY

In accordance with one embodiment of the present disclosure, a forceps is provided, the forceps includes a pair of shaft members each having a jaw member disposed at a distal end thereof. One (or both) of the shaft members is moveable relative to the other about a pivot pin between a spaced-apart position and a first approximated position to move the jaw members between an open position and a closed position. A knife assembly is also provided. The knife assembly includes a knife blade and one or more actuator arms. The knife blade is mechanically keyed to the pivot pin and moveable between an initial position, wherein the knife blade is disposed within one of the jaw members, and an extended position, wherein the knife blade extends between the jaw members. The actuator arm(s) are likewise mechanically keyed to the pivot pin and extend therefrom. The actuator arm(s) is moveable between an un-actuated position and an actuated position to rotate the pivot pin relative to the jaw members to move the knife blade between the initial position and the extended position.

In one embodiment, the actuator arm(s) is coupled to a spring at an end thereof. The spring is moveable between an at-rest position and an extended position to move the actuator arm(s) between the un-actuated position and the actuated position, e.g., to move the knife blade between the initial position and the extended position. More specifically, the spring may be configured to move from the at-rest position to the extended position upon movement of the shaft members to a second approximated position. Further, the spring may be engaged to one of the shaft members at an end thereof and to the actuator arm(s) at an opposite end thereof.

In another embodiment, a first cam slot is defined within one of the shaft members and a second cam slot is defined within the actuator arm(s). A cam pin is disposed through each of the first and second cam slots and is coupled to the distal end of the spring, such that, upon movement of the shaft members to the second approximated position, the spring is moved from the at-rest position to the extended position to translate the cam pin along the first and second cam slots, thereby moving the actuator arm(s) to the actuated position, thus moving the knife blade to the extended position. Further, the forceps may be configured such that, upon movement of the shaft members to the second approximated position, one of the shaft members contacts the spring and urges the spring to move from the at-rest position to the extended position.

In yet another embodiment, one (or both) of the jaw members includes a jaw frame fixedly engaged to the respective shaft member and a disposable jaw housing releasably engageable with the jaw frame. Additionally, a seal plate may be releasably engaged to the jaw housing. The seal plate may include a longitudinally-extending blade channel defined therethrough. The blade channel is configured to permit passage of the knife blade therethrough upon movement of the knife blade from the initial position to the extended position. Further, the seal plate may be adapted to connect to a source of electrosurgical energy, e.g., for energizing the seal plate.

In still another embodiment, the jaw housing includes one or more engagement features configured to releasably engage a complementary engagement feature (or features) defined within the jaw frame.

In still yet another embodiment, the shaft members, the pivot pin, and the knife assembly are releasably engaged to one another, e.g., such that the shaft members, the pivot pin and the knife assembly may be assembled and disassembled by the user.

A method of assembling a forceps, e.g., the forceps according to any of the embodiments discussed above, is also provided in accordance with the present disclosure. The method includes providing a pair of shaft members, each shaft member having a jaw member disposed at a distal end thereof, providing a pivot pin including first and second mechanical keying features, and providing a knife assembly. The knife assembly includes a knife blade having a first complementary mechanical keying feature and one or more actuator arm(s) having a second complementary mechanical keying feature. The method further includes pivotably coupling the pivot pin to the shaft members such that the shaft members are movable between a spaced-apart position and a first approximated position to move the jaw members between an open position and a closed position, engaging the first mechanical keying feature of the pivot pin with the first complementary mechanical keying feature of the knife blade, and engaging the second mechanically keying feature of the pivot pin with the second complementary mechanical keying feature of the actuator arm(s). As such, when the forceps is assembled as described above, movement of the actuator arm(s) from an un-actuated position to an actuated position may be effected to rotate the pivot pin relative to the jaw members, thereby moving the knife blade from an initial position, wherein the knife blade is disposed within one of the jaw members, to an extended position, wherein the knife blade is extended between the jaw members.

In one embodiment, one (or both) of the jaw members includes a jaw frame fixedly engaged to the respective shaft member and a disposable jaw housing releasably engageable with the jaw frame. In such an embodiment, the method may further include releasably engaging the disposable jaw housing to the jaw frame.

In another embodiment, the method includes releasably engaging a seal plate to the jaw housing. Further, the seal plate may be connected to a source of electrosurgical energy, e.g., via an electrosurgical cable.

In yet another embodiment, the method includes coupling a proximal end of the actuator arm(s) to a proximal end of one of the shaft members. More specifically, a cam pin may be inserted through a first cam slot defined within one of the shaft members and through a second cam slot defined within the actuator arm(s) to couple the actuator arm(s) to the shaft member. Accordingly, upon movement of the shaft members to a second approximated position, the cam pin is translated along the first and second cam slots, thereby moving the actuator arm(s) from the un-actuated position to the actuated position, e.g., to move the knife blade from the initial position to the extended position.

In still another embodiment, the method includes providing a spring having a proximal end and a distal end, coupling the cam pin to the distal end of the spring, and coupling the proximal end of the spring to a proximal end of one of the shaft members. The spring is configured for movement from an at-rest position to an extended position upon movement of the shaft members to the second approximated position to move the actuator arm(s) from the un-actuated position to the actuated position, e.g., to move the blade from the initial position to the extended position.

A method of assembling a jaw member is also provided in accordance with the present disclosure. The jaw member to be assembled may be any of the jaw members discussed above, e.g., a jaw member including a jaw frame, a jaw housing, an insulator, and an electrically-conductive seal plate. The method includes positioning the seal plate about the insulator, slidably positioning the jaw housing about the seal plate and the insulator such that the jaw housing, the seal plate, and the insulator are retained in fixed relation relative to one another, and releasably engaging the jaw housing to the jaw frame to retain the jaw housing, the seal plate, the insulator, and the jaw frame in fixed relation relative to one another.

In one embodiment, jaw housing includes a track defined therein. The seal plate includes a pair of wings configured to slidably engage the track of the jaw housing to secure the seal plate, the jaw housing, and the insulator to one another.

In another embodiment, the insulator is formed partially (or entirely) from a resiliently compressible material. The insulator is configured to be compressed from an initial state to a compressed state upon positioning of the jaw housing about the seal plate and the insulator. As such, the biasing force acting of the insulator, e.g., biasing the insulator back toward the initial state, frictionally retains the jaw housing, the seal plate, and the insulator in fixed relation relative to one another, once the jaw member is assembled.

BRIEF DESCRIPTION OF THE DRAWINGS

Various embodiments of the subject instrument are described herein with reference to the drawings wherein.

DETAILED DESCRIPTION

Figure 1:
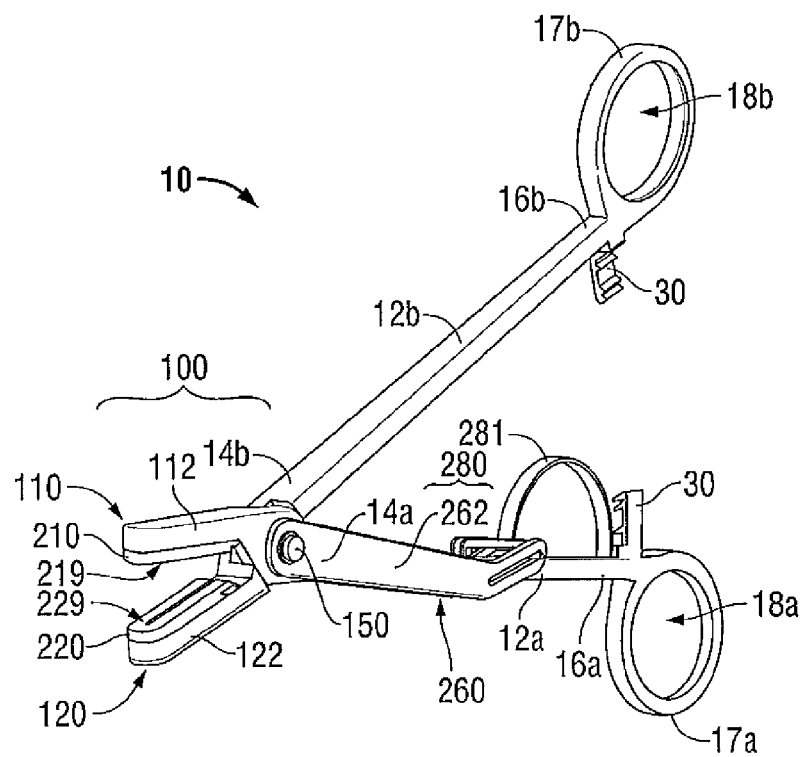
FIG. 1 is a front, perspective view of one embodiment of a forceps provided in accordance with the present disclosure wherein the forceps is shown in an open position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
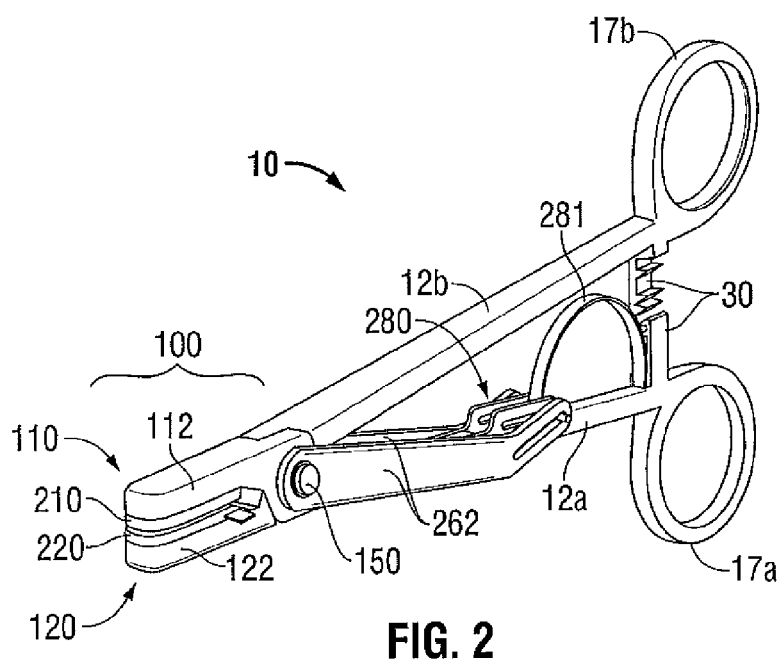
FIG. 2 is a front, perspective view of the forceps of FIG. 1 shown in a closed position.

Referring initially to FIGS. 1 and 2, a forceps 10 is shown including two elongated shafts 12a and 12b each having a distal end 14a and 14b and a proximal end 16a and 16b, respectively. An end effector assembly 100 including opposing jaw members 110, 120, is attached to distal ends 14a and 14b of shafts 12a and 12b, respectively. Opposing jaw members 110 and 120 are pivotably connected about a pivot pin 150 and are moveable relative to one another between an open position (FIG. 1) and a closed position (FIG. 2), upon movement of shaft members 12a and 12b between a spaced-apart position (FIG. 1) and a first approximated position (FIG. 2), for grasping tissue therebetween. Further, each jaw member 110, 120 includes a disposable component 210, 220, respectively, that is releasably engaged thereon. Although forceps 10 is shown as an open surgical forceps, jaw members 110, 120 including disposable components 210, 220, respectively, may similarly be configured for use with an endoscopic surgical forceps (not shown).

Figure 14A:
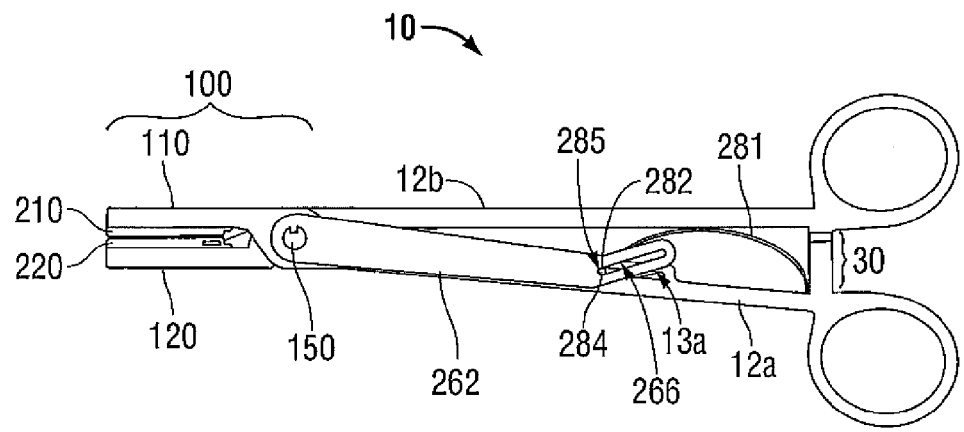
FIG. 14A is a side view of the forceps of FIG. 1 shown in the closed position, wherein the knife blade is in the extended position.
Figure 14B:
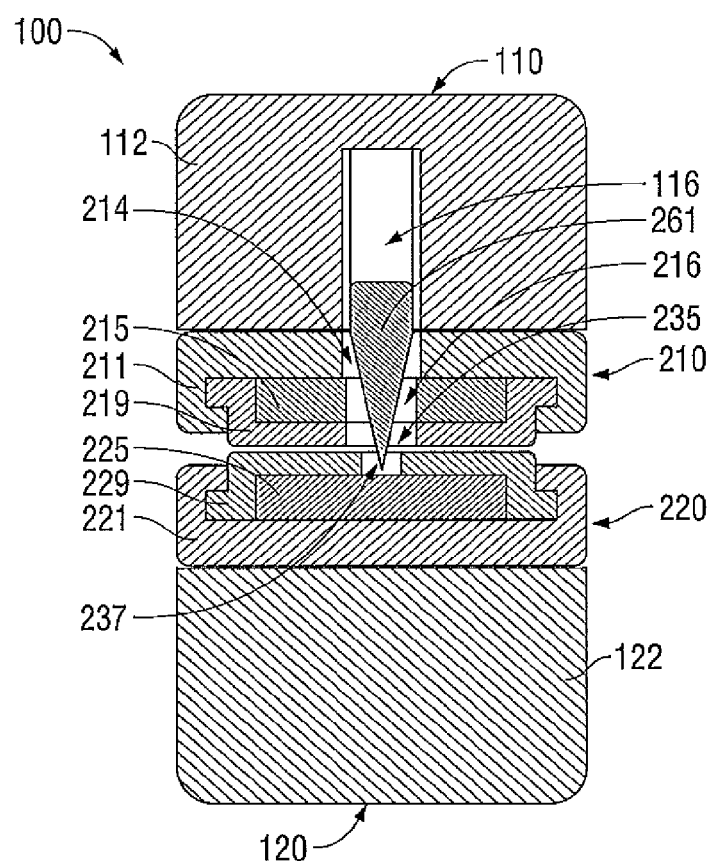
FIG. 14B is a transverse, cross-sectional view of the forceps of FIG. 1 shown in the closed position, wherein the knife blade is in the extended position.

With continued reference to FIGS. 1 and 2, each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of shafts 12a and 12b relative to one another which, in turn, pivots jaw members 110 and 120 between the open position (FIG. 1) and the closed position (FIG. 2), wherein the jaw members 110 and 120 cooperate to grasp tissue therebetween. Further, as will be described in greater detail below, shafts 12a, 12b are moveable between a spaced-apart position (FIG. 1), a first approximated position for closing jaw members 110, 120 to grasp tissue therebetween (FIG. 2), and a second approximated position for advancing knife blade 261 of knife assembly 260 (FIGS. 9-11) between jaw members 110, 120 to cut tissue grasped therebetween (FIGS. 14A-14B).

A ratchet 30 may be included for selectively locking jaw members 110, 120 relative to one another at various positions during pivoting. The ratchet 30 may include graduations or other visual markings that enable the user to easily and quickly ascertain and control the amount of closure force between the jaw members 110 and 120.

Figure 3:
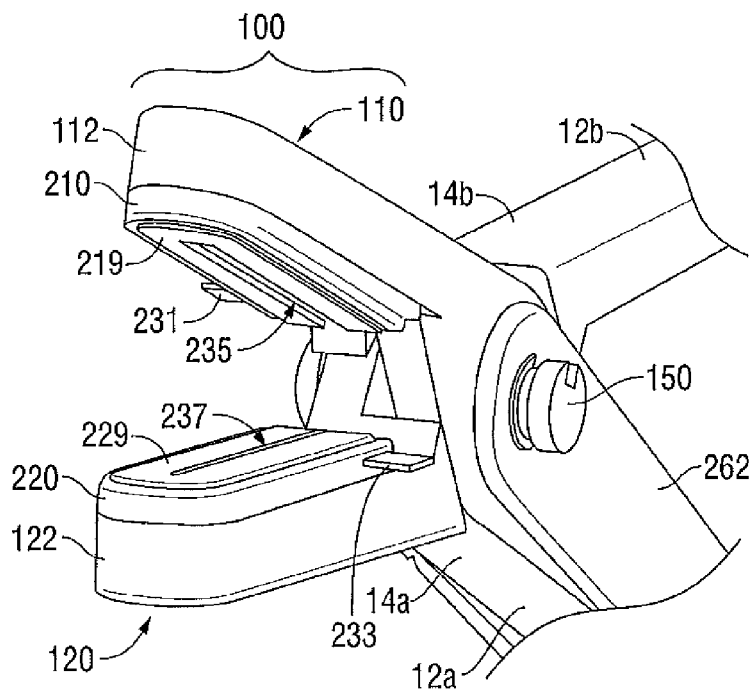
FIG. 3 is a greatly-enlarged, perspective view of the end effector assembly of the forceps of FIG. 1.
Figure 4:
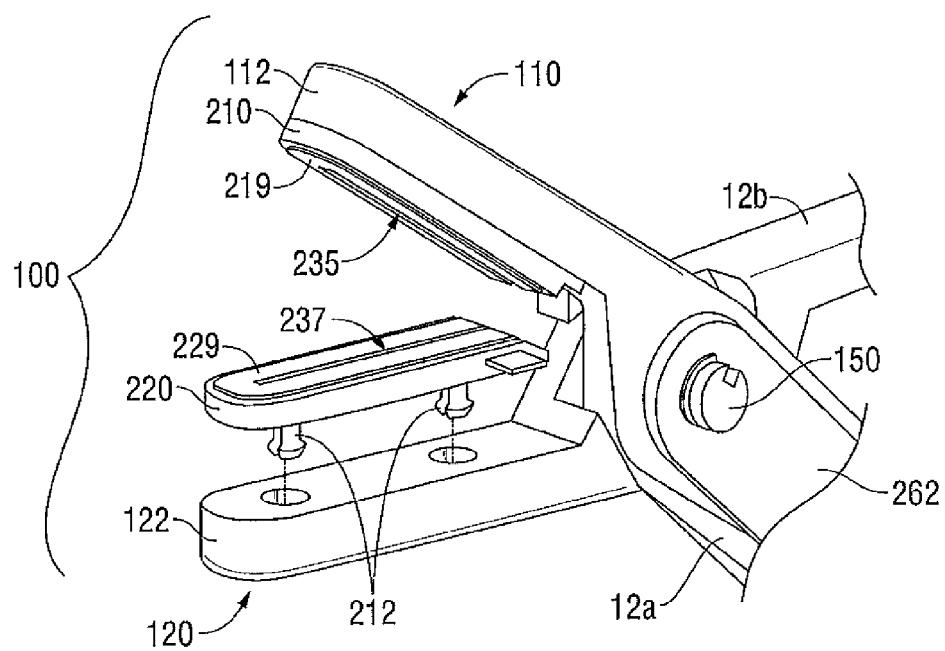
FIG. 4 is a greatly-enlarged, perspective view of the end effector assembly of the forceps of FIG. 1 showing a disposable component positioned for engagement with one of the jaw members of the end effector assembly.

Turning now to FIGS. 3-4, in conjunction with FIGS. 1 and 2, and as mentioned above, forceps 10 includes a pair of jaw members 110, 120. Jaw members 110, 120 each include a disposable component 210, 220 that is releasably engageable with a jaw frame 112, 122, respectively. Jaw frames 112, 122 of jaw members 110, 120, respectively, are fixedly engaged to the respective shafts 12a, 12b, e.g., each jaw frame 112, 122 is formed as a single component with the respective shaft 12a, 12b. Disposable components 210, 220, are removeable from jaw frames 112, 122, respectively, and are replaceable with new disposable components 210, 220, e.g., disposable components are configured to be discarded and replaced after a single use (or a single procedure), while shafts 12a, 12b and their respective jaw frames 112, 122, are formed from a sterilizable material, e.g., stainless steel, such that they may be sterilized, e.g., placed in an autoclave, after each procedure for repeated use. As will be described in greater detail below, forceps 10 further includes a disposable knife assembly 260 (see FIG. 9) that is releasably engageable therewith (although knife assembly 260 may alternatively be configured as a sterilizable and, thus, reusable component). As can be appreciated, requiring only a new set of disposable components 210, 220 and knife assembly 260 (FIG. 9), rather than an entire new surgical instrument, helps reduce the equipment costs associated with performing a particular surgical procedure.

Figure 5:
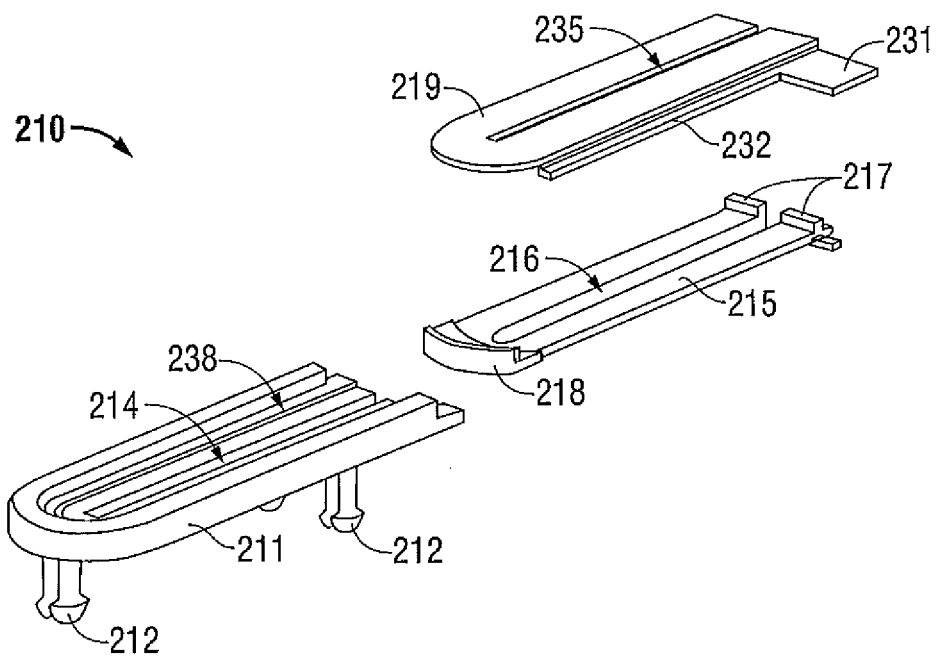
FIG. 5 is an exploded, perspective view of the disposable component of one of the jaw members of the forceps of FIG. 1.
Figure 6:
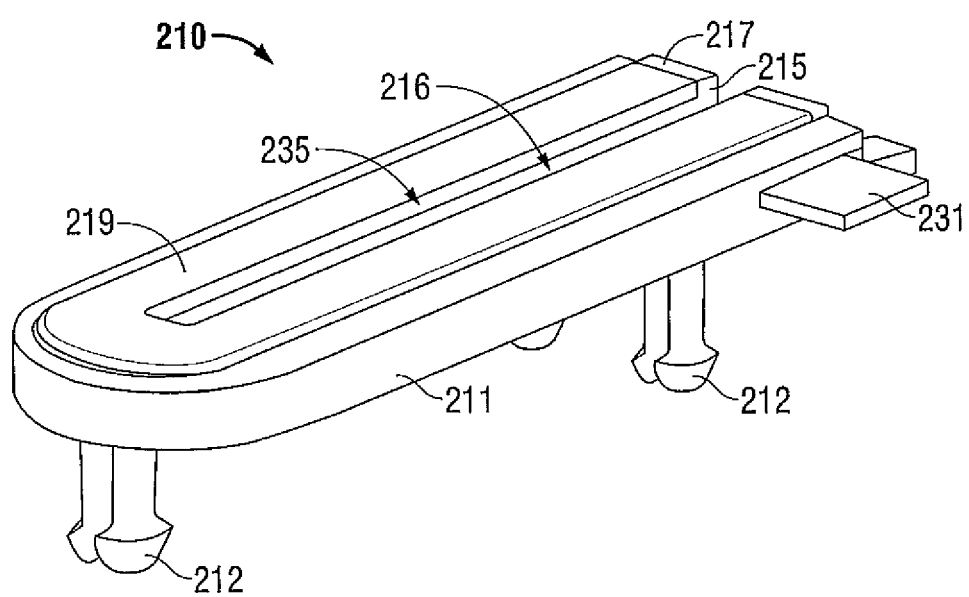
FIG. 6 is a front, perspective view of the disposable component of FIG. 5, shown as assembled.

With reference now to FIGS. 5-6, disposable component 210 of jaw member 110 will be described. Disposable component 210 generally includes an insulative jaw housing 211, an insulator 215, and an electrically-conductive tissue sealing plate 219. Jaw housing 211 defines a generally horseshoe or U-shaped configuration forming an elongated aperture 214 extending longitudinally at least partially therethrough. As will be described in greater detail below, knife blade 261 of knife assembly 260 (FIGS. 9-10) is configured for positioning within elongated aperture 214 of jaw housing 211 when in an initial position. Knife blade 261 (FIGS. 9-10) is moveable from the initial position within jaw housing 211 to an extended position, wherein knife blade 261 extends between jaw members 110, 120 to cut tissue grasped therebetween. Jaw housing 211 is further configured to mechanically engage insulator 215 and tissue sealing plate 219, e.g., in slidable snap-fit engagement therewith, although other mechanisms (not shown) for releasably securing jaw housing 211 about insulator 215 and tissue sealing plate 219 may be provided. The assembly of the disposable components 210, 220 of jaw members 110, 120, respectively, will be described in greater detail below.

Figure 10:
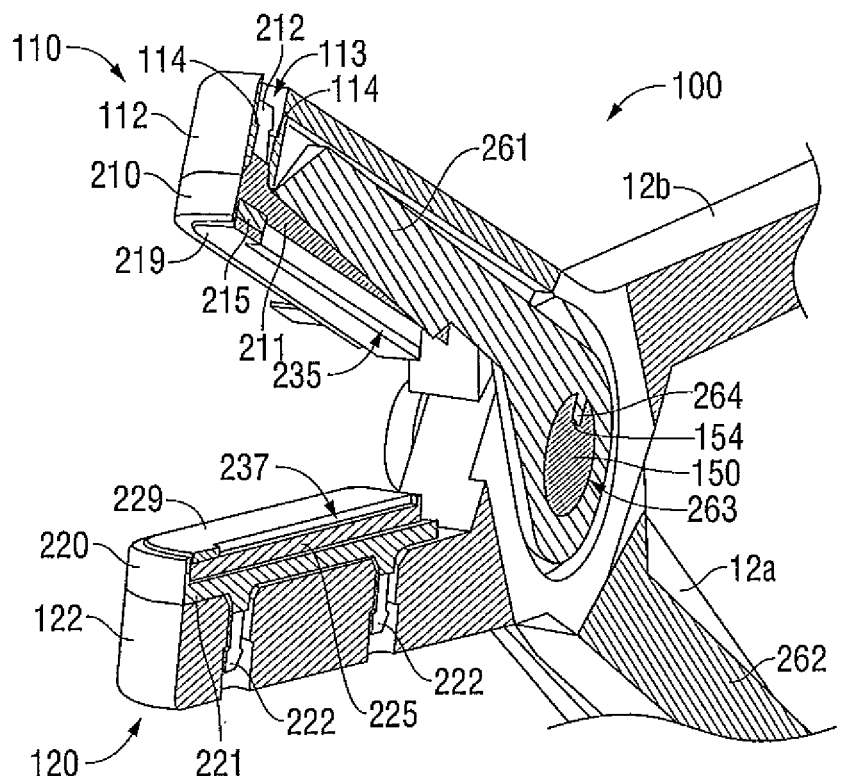
FIG. 10 is a perspective, longitudinal, cross-sectional view of the end effector assembly of the forceps of FIG. 1 showing the knife blade in an initial position.

Continuing with reference to FIGS. 5-6, jaw housing 211 includes one or more engagement features, e.g., flexible, snap-fit protrusions 212, extending therefrom and configured to releasably engage jaw housing 211 to jaw frame 112 of jaw member 110 (see FIG. 10). More specifically, flexible, snap-fit protrusions 212 of jaw housing 211 are configured for insertion through complementary-shaped apertures 113 defined within jaw frame 112 (see FIG. 10) such that jaw housing 211 may be releasably secured to jaw frame 112. Further, protrusions 212 disposed on jaw housing 211 may be longitudinally and laterally offset relative to one another such that tilting, rotating, or other movement of disposable component 210 relative to jaw frame 112 is substantially inhibited once disposable component 210 is engaged to jaw frame 112.

Figure 13A:
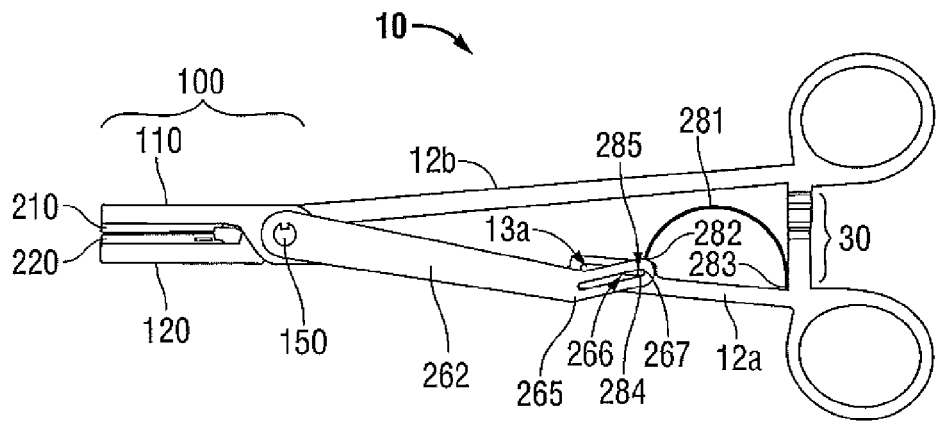
FIG. 13A is a side view of the forceps of FIG. 1 shown in the closed position, wherein the knife blade is in the initial position.
Figure 13B:
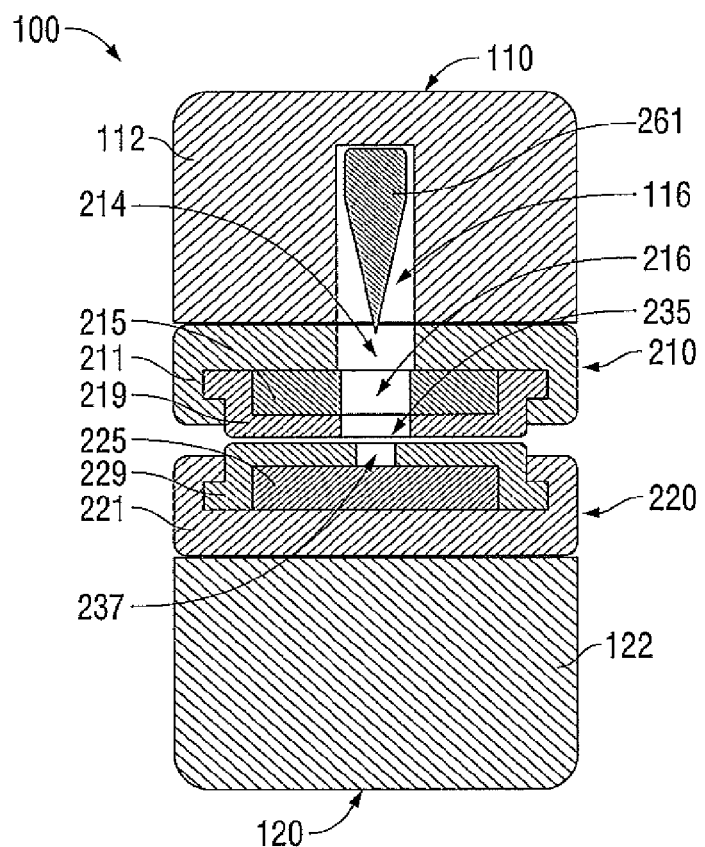
FIG. 13B is a transverse, cross-sectional view of the forceps of FIG. 1 shown in the closed position, wherein the knife blade is in the initial position.

Jaw frame 112, as best shown in FIGS. 13B and 14B, and as will be described in greater detail below, may include a blade slot 116 defined therein and extending longitudinally therealong. Blade slot 116 is configured to align with elongated aperture 214 of jaw housing 211 upon engagement of jaw housing 211 to jaw frame 112 and is similarly configured to permit positioning of knife blade 261 of knife assembly 260 therein when knife blade 261 is disposed in the initial position. Accordingly, when knife blade 261 is moved from the initial position to the extended position, knife blade 261 extends through blade slot 116 of jaw frame 112 and through elongated aperture 214 of jaw housing 211 such that knife blade 261 is extended between jaw members 110, 120 to cut tissue grasped therebetween.

During assembly, as best shown in FIGS. 5-6 and 10, flexible, snap-fit protrusions 212 of jaw housing 211 are aligned with apertures 113 of jaw frame 112. Next, jaw housing 211 and jaw frame 112 are approximated relative to one another until tabs 213 disposed on the free ends of flexible, snap-fit protrusions 212 of jaw housing 211 snap into engagement with notches 114 defined within the interior surfaces of apertures 113 of jaw frame 112. An audible and/or tactile "snap," or other feedback signal, may be provided to alert the user that jaw housing 211 has been securely engaged within jaw frame 112.

In order to disengage jaw housing 211 from jaw frame 112, jaw housing 211 and jaw frame 112 are pulled apart from one another with sufficient force such that tabs 213 of flexible snap-fit protrusions 212 of jaw housing 211 are disengaged from notches 114 of apertures 113 of jaw frame 112, allowing jaw housing 211 to be removed from jaw frame 112. Similarly as described above, an audible and/or tactile "snap," or other feedback signal, may alert the user that jaw housing 211 has been disengaged from jaw frame 112.

Referring once again to FIGS. 5-6, insulator 215 is formed at least partially from an electrically-insulative material and is configured to electrically isolate tissue sealing plate 219 from the remaining components of jaw member 110. Insulator 215 is slidably disposable within jaw housing 211 and is configured to mechanically engage tissue sealing plate 219 thereon. Similar to jaw frame 112 and jaw housing 211, insulator 215 also includes a blade channel 216 extending longitudinally therethrough to permit passage of knife blade 261 (see FIGS. 13B and 14B). Proximal base 217 of insulator 215 is configured to abut the proximal end of tissue sealing plate 219 to retain tissue sealing plate 219 in position within jaw housing 211 once insulator 215 and tissue sealing plate 219 have been slidably engaged therein. Additionally, insulator 215 may be formed at least partially from a compressible material, e.g., silicon, that is compressed upon insertion of insulator 215 into jaw housing 211 such that insulator 215 and tissue sealing plate 219 may be frictionally retained within jaw housing 211.

Electrically-conductive tissue sealing plate 219, as mentioned above, is disposed about insulator 215. Tissue sealing plate 219 includes a lateral flange 231 extending therefrom that is configured to electrically connect tissue sealing plate 219 to a source of electrosurgical energy such as an electrosurgical generator (not shown), e.g., via an electrosurgical cable (not shown). As will be described in greater detail below, disposable component 220 of jaw member 120 may similarly include an electrically-conductive tissue sealing plate 229 (see FIGS. 7-8) such that electrosurgical energy may be selectively supplied to either or both of the electrically conductive tissue sealing plates 219, 229 of disposable components 210, 220 of jaw members 110, 120, respectively, to seal tissue grasped between jaw members 110 and 120. Further, either (or both) of tissue sealing plates 219, 229 may include lateral flanges 231, 233, respectively, configured to connect tissue sealing plates 219, 229 to a source of energy to supply energy thereto. Alternatively, other suitable mechanisms (not shown) for electrically coupling tissue sealing plates 219, 229 to a source of energy may be provided.

With continued reference to FIGS. 5-6, tissue sealing plate 219 of disposable component 210 of jaw member 110 may include a longitudinally-extending blade channel 235 defined therein. Blade channel 235 is configured to align with blade channel 216 defined within insulator 215, elongated aperture 214 defined within jaw housing 211, and blade slot 116 defined within jaw frame 112 to permit passage of knife blade 261 of knife assembly 260 (see FIGS. 13B and 14B) therethrough upon movement of knife blade 261 from the initial position (FIG. 13A) to the extended position (FIG. 13B). Blade channel 235 may further be configured to facilitate and/or enhance cutting of tissue upon extension of knife blade 261 therethrough.

Continuing with reference to FIGS. 5-6, disposable component 210 of jaw member 110 may come preassembled, e.g., jaw housing 211, insulator 215 and tissue sealing plate 219 may be engaged to one another during manufacturing, or may be configured to be assembled by the user. In either embodiment, disposable component 210 and/or the sub-components thereof (e.g., jaw housing 211, insulator 215 and/or tissue sealing plate 219) may define various configurations such that the user may select a particular disposable component 210 (or sub-component thereof) suitable for the particular surgical procedure to be performed. For example, different disposable components 210 (or the subcomponents thereof) may be configured to define various dimensions, may be formed from various materials, and/or may have various other features to facilitate mechanical, electrical, or frictional tissue dissection and/or tissue sealing of a wide range of tissue sizes and compositions. Other variations are also contemplated. Put more generally, the interchangeability of different disposable components 210 configured for use with forceps 10 permits the user to customize forceps 10 for use in a wide-range of surgical procedures by selecting a particular disposable component 210 (or subcomponent thereof) suitable for the particular surgical procedure. As can be appreciated, such a configuration reduces the overall number of different surgical instruments needed to perform a wide-range of surgical procedures, thereby helping to reduce overall equipment costs, which, in turn, helps reduce the costs associated with each surgical procedure.

Figure 7:
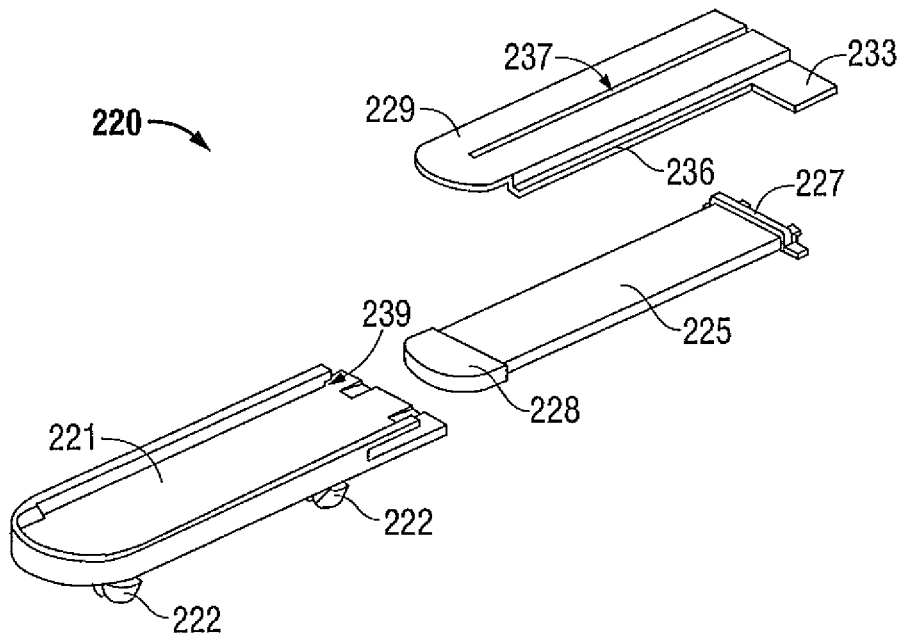
FIG. 7 is an exploded, perspective view of the disposable component of the other jaw member of the forceps of FIG. 1.
Figure 8:
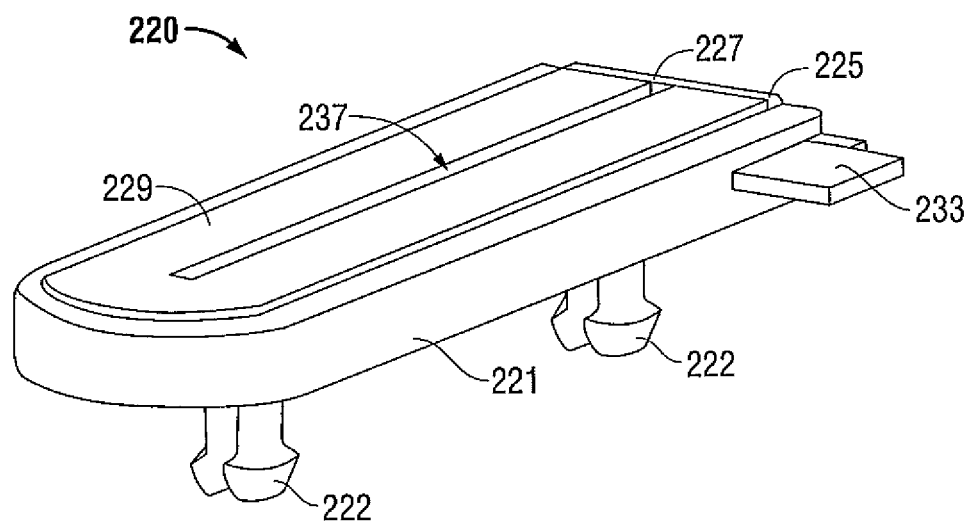
FIG. 8 is a front, perspective view of the disposable component of FIG. 7, shown as assembled.

Turning now to FIGS. 7-8, disposable component 220 of jaw member 120 will be described. Disposable component 220 of jaw member 120 is similar to disposable component 210 of jaw member 110 and includes an insulative jaw housing 221, an insulator 225, and a tissue sealing plate 229. Jaw housing 221 is configured to mechanically engage insulator 225 and tissue sealing plate 229 in slidable snap-fit engagement therewith, although other mechanisms (not shown) are contemplated. Similar to jaw housing 211, jaw housing 221 includes one or more flexible, snap-fit protrusions 222 configured to releasably engage jaw housing 221 to jaw frame 122 of jaw member 120 (see FIG. 10). An audible and/or tactile "snap," or other feedback signal, may be provided to alert the user as to the engagement (or disengagement) of jaw housing 221 and jaw frame 122.

With continued reference to FIGS. 7-8, insulator 225 is similar to insulator 215 of disposable component 210 of jaw member 110 (see FIGS. 5-6) and is formed at least partially from an electrically-insulative material that is configured to electrically isolate tissue sealing plate 229 from the remaining components of jaw member 120. Insulator 225 is slidably disposable within jaw housing 221 and is configured to mechanically engage tissue sealing plate 229 thereon. When disposable component 220 is assembled, proximal base 227 of insulator 225 abuts the proximal end of tissue sealing plate 229 to retain tissue sealing plate 229 in position within jaw housing 221. Similarly as discussed above with regard to disposable component 210 (FIGS. 5-6), insulator 225 may be formed at least partially from a compressible material, e.g., silicon, such that insulator 225 and tissue sealing plate 229 may be frictionally retained within jaw housing 221.

As shown in FIGS. 7-8, tissue sealing plate 229 is configured to sit atop insulator 225 and to mechanically engage jaw housing 221. More specifically, with tissue sealing plate 229 disposed about insulator 225, insulator 225 and tissue sealing plate 229 may be sildably positioned within jaw housing 221. Upon slidable positioning of insulator 225 and tissue sealing plate 229 within jaw housing 221, proximal base 227 of insulator 225 may be configured to snap-fittingly engage jaw housing 221 to securely retain insulator 225 within jaw housing 221, while proximal base 227 of insulator 225 abuts the proximal end of tissue sealing plate 229 to retain tissue sealing plate 229 in position within jaw housing 221. Additionally, insulator 225 may be formed at least partially from a compressible material to frictionally engage jaw housing 221, insulator 225 and tissue sealing plate 229 of disposable component 220 to one another.

Tissue sealing plate 229 may further include a longitudinally-extending blade channel 237 defined at least partially therethrough that permits extension of knife blade 261 of knife assembly 260 therethrough (see FIG. 10) upon extension of knife blade 261 to the extended position. Blade channel 237 may be configured to facilitate and/or enhance cutting of tissue during extension of knife blade 261 therethrough (FIG. 10). As discussed above, tissue sealing plate 229 may also include a lateral flange 233 adapted to connect tissue sealing plate 229 to a source of electrosurgical energy for energizing tissue sealing plates 219, 229 of jaw members 110, 120, respectively.

Jaw housing 221, insulator 225, and/or tissue sealing plate 229 may otherwise be configured similarly to jaw housing 211, insulator 215, and tissue sealing plate 219, respectively, of disposable component 210 of jaw member 110, discussed above (see FIGS. 5A-5C). Further, although jaw frame 112 and disposable component 210 are shown configured to retain knife blade 261 of knife assembly 260 (FIGS. 9-10) therein when knife blade 261 is disposed in the initial position, this configuration may be reversed, e.g., such that jaw frame 122 and disposable component 220 of jaw member 120 are configured to retain knife blade 261 of knife assembly 260 therein (FIGS. 9-10).

Similar to disposable component 210, discussed above, disposable component 220 may come preassembled, e.g., disposable component 220 may be assembled during manufacturing, or may be configured to be assembled by the user. In either embodiment, similarly as discussed above, disposable component 220 and/or the sub-components thereof (e.g., jaw housing 221, insulator 225 and/or tissue sealing plate 229) may define various configurations such that the user may select a particular disposable component 220 (or sub-component thereof) suitable for the particular surgical procedure to be performed.

Figure 9:
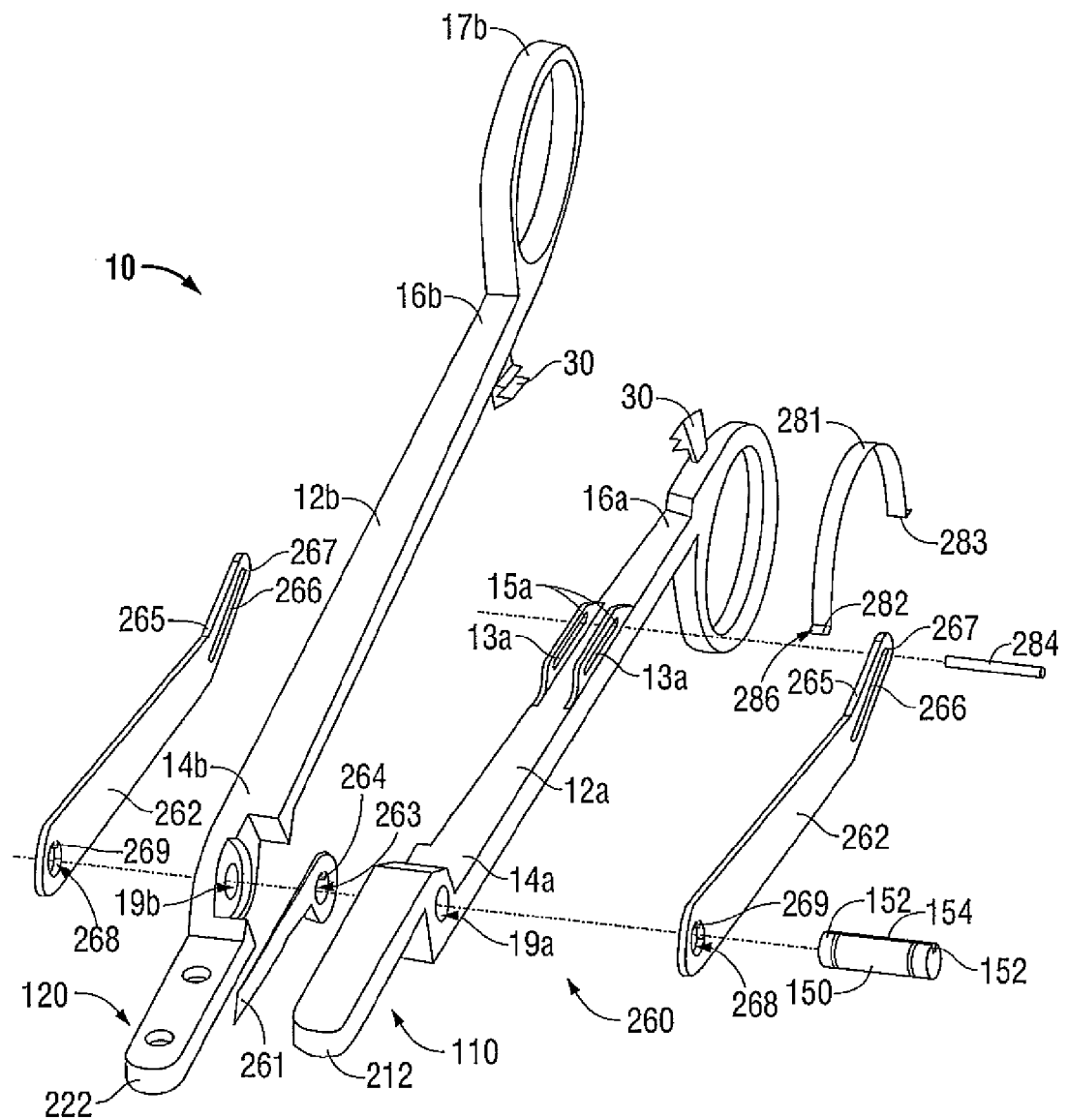
FIG. 9 is an exploded, perspective view of the forceps of FIG. 1.
Figure 11:
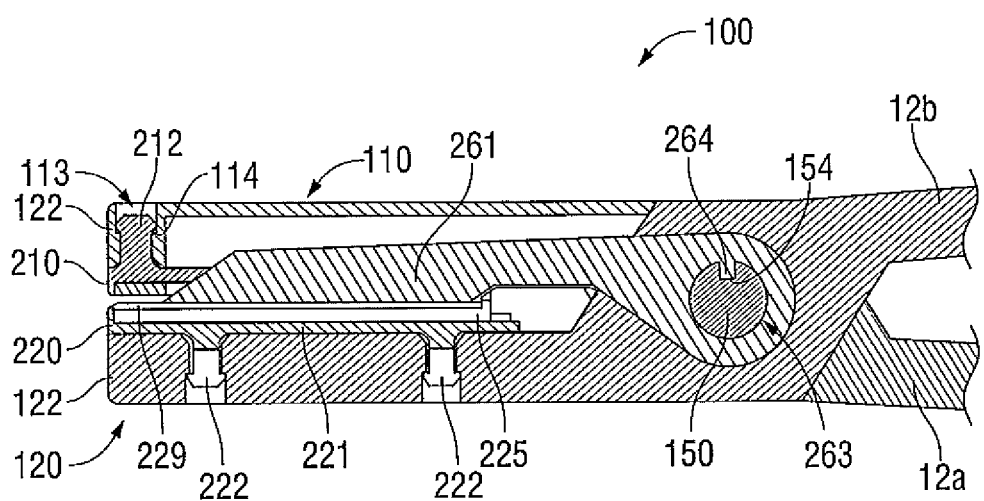
FIG. 11 is a side, longitudinal, cross-sectional view of the end effector assembly of the forceps of FIG. 1 showing the knife blade in an extended position.

Turning now to FIGS. 9-11, in conjunction with FIGS. 1 and 2, knife assembly 260 will be described. Knife assembly 260 is configured for releasable coupling to forceps 10 such that a user may assemble, disassemble, and reassemble forceps 10, e.g., to sterilize the reusable portions and replace the disposable portions of forceps 10 in preparation for reuse of forceps 10. However, forceps 10, including knife assembly 260, may also be configured as a fully-assembled instrument, e.g., where forceps 10 is permanently assembled at the time of manufacturing.

As best shown in FIG. 9, knife assembly 260 generally includes a knife blade 261, one or more actuator arms 262, e.g., two actuator arms 262, and a spring-cam mechanism 280 (FIGS. 1-2). As shown in FIG. 9, knife assembly 260 includes two actuator arms 262 positioned on either side of shaft 12a, although only one actuator arm 262 need be provided. Actuator arms 262 are coupled to knife blade 261 via pivot pin 150, such that, as will be described in greater detail below, movement of actuator arms 262 between an un-actuated position (FIG. 13A) and an actuated position (FIG. 14A) rotates pivot pin 150 relative to jaw members 110, 120 to move knife blade 261 between the initial position (FIG. 13B) and the extended position (FIG. 14B).

Figure 12:
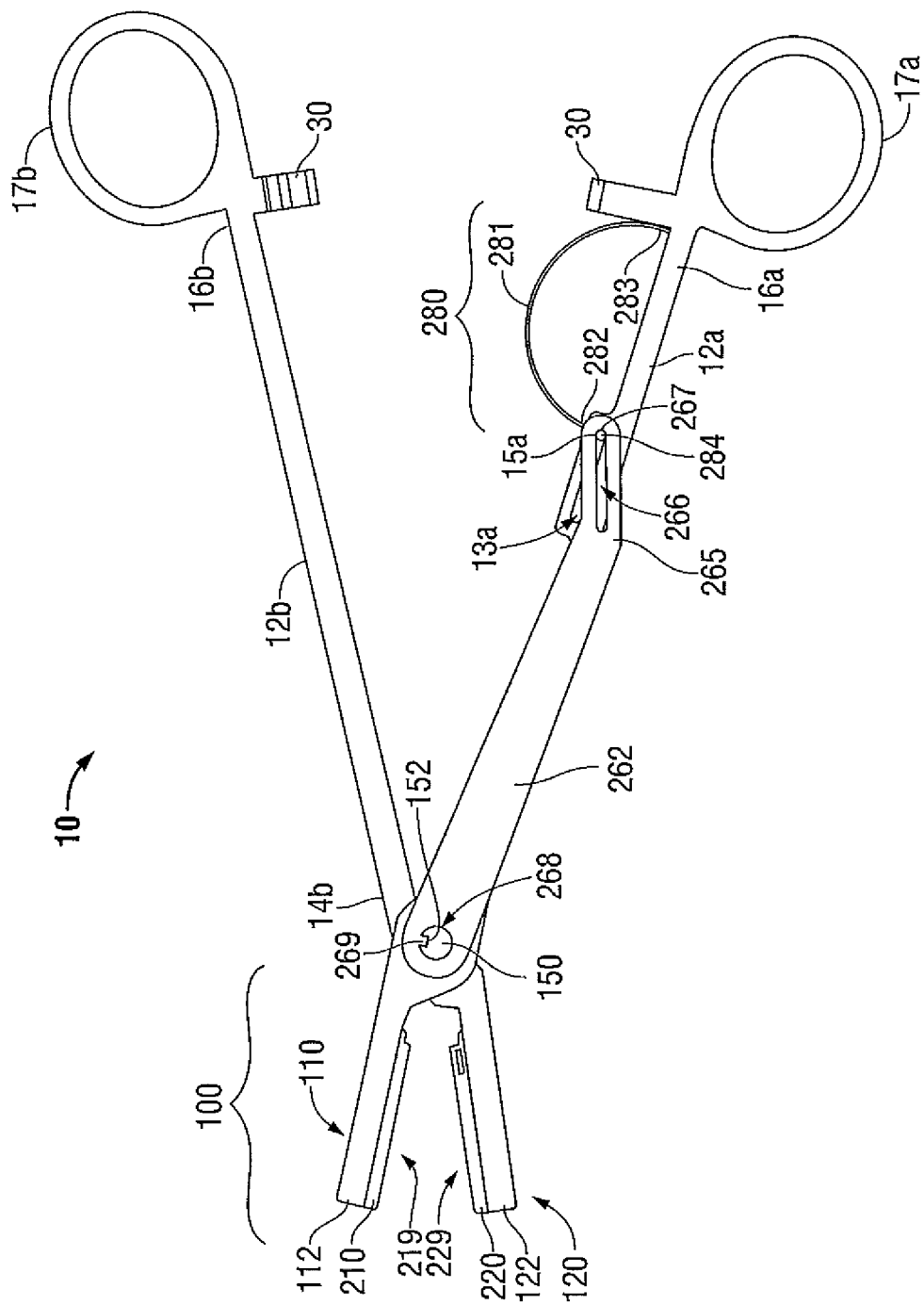
FIG. 12 is a side view of the forceps of FIG. 1 shown in the open position.

Referring again to FIGS. 9-11, in conjunction with FIGS. 1 and 2, actuator arms 262 extend proximally from pivot pin 150 along shaft 12a (although actuator arms 262 may alternatively be configured to extend along shaft 12b). More specifically, each actuator arm 262 includes a distal aperture 268 defined therein for engaging pivot pin 150 therethrough. As best shown in FIG. 12, pivot pin 150 and actuator arms 262 each define complementary mechanical keying features, e.g., notches 152 and protrusions 269, respectively, configured to engage one another such that rotation of actuator arms 262 about pivot pin 150 effects similar rotation of pivot pin 150 relative to jaw members 110, 120 of end effector assembly 100. As shown in the Figures, pivot pin 150 includes notches 152 defined within an outer peripheral surface thereof, each notch 152 is configured for engaging a complementary-shaped protrusion 269 of each actuator arm 262, which extend inwardly into distal apertures 268 of actuator arms 262. However, the number, size, shape and/or configuration of the complementary mechanical keying features of pivot pin 150 and actuator arms 262 may be varied so long as pivot pin 150 and actuator arms 262 are engaged to one another such that rotation of actuator arms 262 about pivot pin 150 effects similar rotation of pivot pin 150 relative to jaw members 110, 120 of end effector assembly 100.

With continued reference to FIGS. 9-11, and in particular to FIG. 9, knife blade 261 of knife assembly 260 likewise includes a mechanical keying feature, e.g., protrusion 264, extending into a proximal aperture 263 thereof for engaging a complementary mechanical keying feature, e.g., notch 154, of pivot pin 150 upon insertion of pivot pin 150 through proximal aperture 263 of knife blade 261. Similarly as discussed above, due to the mechanically-keyed engagement between protrusion 264 of knife blade 261 and notch 154 of pivot pin 150, rotation of pivot pin 150 relative to jaw members 110, 120 effects similar rotation of knife blade 261 about pivot pin 150. As such, with actuator arms 262 and pivot pin 150 mechanically-keyed to one another, and with pivot pin 150 and knife blade 261 mechanically-keyed to one another, actuator arms 262 may be rotated about pivot pin 150, e.g., between the un-actuated position (FIG. 13A) and the actuated position (FIG. 14A), to rotate knife blade 261 about pivot pin 150 and relative to jaw members 110, 120, e.g., between the initial position (FIG. 13B) and the extended position (FIG. 14B). As will be described in greater detail below, during assembly, actuator arms 262 and knife blade 261 are configured to be engaged to pivot pin 150 such that the initial position of knife blade 261, e.g., wherein knife blade 261 is disposed within jaw member 110, corresponds to the un-actuated position of actuator arms 262.

Referring momentarily to FIGS. 1-2, although pivot pin 150 is configured to engage knife blade 261 and actuator arms 262 of knife assembly 260 in mechanically-keyed engagement, pivot pin 150 need not be mechanically-keyed to shafts 12a, 12b. In other words, shafts 12a and 12b are free to pivot relative to one another about and relative to pivot pin 150 between the spaced-apart position and the first approximated position for moving jaw members 110, 120 between the open and closed positions for grasping tissue therebetween, while knife blade 261 and actuator arms 262 of knife assembly 260 remain disposed in the initial and un-actuated positions, respectively. As will be described in greater detail below, shafts 12a, 12b may then be moved to the second approximated position to move actuator arms 262 to the actuated position to rotate pivot pin 150 relative to jaw members 110, 120 and to thereby move knife blade 261 from the initial position to the extended position to cut tissue grasped between jaw members 110, 120. Alternatively, pivot pin 150 may be mechanically-keyed to one or both of jaw members 110, 120 such that moving shafts 12a, 12b between the spaced-apart and approximated positions closes jaw members 110, 120 to grasp tissue and, thereafter, extends knife blade 261 therebetween to cut tissue.

Turning once again to FIGS. 9-11, in conjunction with FIGS. 1-2, actuator arms 262 of knife assembly 260 each define an angled proximal portion 265 that includes an angled cam slot 266 defined therein and extending therealong. Further, one of the shafts, e.g., shaft 12a, includes a pair of substantially parallel cam slots 13a defined therein and extending longitudinally therealong adjacent to cam slots 266 of actuator arms 262. More particularly, cam slots 13a of shaft 12a are mis-aligned, or angled relative to cam slots 266 of actuator arms 262 such that the respective cam slots 13a, 266 intersect one another at an intersection position 285 (see FIGS. 13A and 14A).

Continuing with reference to FIGS. 1-2 and 9-11, knife assembly 260 further includes a leaf spring 281, or other biasing member, defining an arch-shaped configuration when at-rest. Proximal end 283 of leaf spring 281 is engaged to shaft 12a and arches therefrom toward shaft 12b before arching back toward shaft 12a to distal end 282 of leaf spring 281. Distal end 282 of leaf spring 281 is coupled to a cam pin 284 that is removably engageable within cam slots 13a, 266, of shaft 12a and actuator arms 262, respectively. As can be appreciated, with cam pin 284 disposed through both cam slots 13a of shaft 12a and cam slots 266 of actuator arms 262, the position of cam pin 284 corresponds to the intersection position 285 of shaft 12a and actuator arms 262.

Initially, as shown in FIGS. 1-2 and FIG. 13A, cam pin 284 is retained at proximal ends 15a, 267 of cam slots 13a, 266, respectively, under the bias of leaf spring 281. In this position, actuator arms 262 are disposed in the un-actuated position. As will be described in greater detail below, as leaf spring 281 is urged from the arched-configuration toward a relatively linear configuration, e.g., upon movement of shafts 12a, 12b to the second approximated position (FIG. 14A), distal end 282 of leaf spring 281 is urged distally along shaft 12a such that cam pin 284 is translated along cam slots 13a, 266 of shaft 12a and actuator arms 262, respectively. As such, due to the angled configuration of cam slot 266 of actuator arms 262 relative to cam slots 13a of shaft 12a, translation of cam pin 284 along cam slots 13a, 266, of shaft 12a and actuator arms 262, respectively, urges actuator arms 262 to rotate about pivot pin 150 and relative to shaft member 12a from the un-actuated position toward the actuated position (see FIG. 14A).

Referring now to FIGS. 1-11, the assembly of forceps 10 will be described. As mentioned above, forceps 10 may be configured to be assembled, disassembled, and reassembled by the user. More particularly, forceps 10 may be configured such that shafts 12a, 12b are sterilizable and reusable, while the remaining components of forceps 10 are disposable after a single use (although some of these components may also be configured as reusable components). Accordingly, since the user is required to discard the old components, sterilize or otherwise prepare the reusable components for reuse, and reload forceps 10 with new disposable components, forceps 10 is configured to be readily assembled and disassembled by a user, as will become more apparent in view of the following. Further, although the follow description by necessity recites the assembly steps of forceps 10 in a particular order, it is envisioned that the following assembly steps of forceps 10 be performed in any suitable order.

With continued reference to FIGS. 1-11, and with reference to FIG. 9 in particular, in order to assemble forceps 10, proximal end 283 of leaf spring 281 is engaged with shaft 12a toward proximal end 16a thereof. More particularly, proximal end 283 of leaf spring 281 may be frictionally engaged within a recess (not explicitly shown) defined between proximal end 16a of shaft 12a and handle 17a or may be secured to shaft 12a in any other suitable fashion such that proximal end 283 of leaf spring 281 is releasably engageable in a fixed position relative to shaft 12a.

Next, cam pin 284 is coupled to distal end 282 of leaf spring 281, e.g., cam pin 284 is inserted through an aperture 286 defined within distal end 282 of leaf spring 281, and is inserted through cam slots 13a, 266, of shaft 12a and actuator arms 262, respectively. Any suitable engagement mechanism (not shown) for securing cam pin 284 within aperture 286 and cam slots 13a, 266 may be provided, e.g., end caps (not shown) may be releasably positioned on opposite ends of cam pin 284.

Next, pivot pin 150 is inserted into position. In order to pivotably engage pivot pin 150 within apertures 19a, 19b, of shafts 12a, 12b, respectively, and to mechanically-key pivot pin 150 in engagement with actuator arms 262 and knife blade 261, distal apertures 268 of actuator arms 262, proximal aperture 262 of knife blade 261 and apertures 19a, 19b of shafts 12a, 12b, respectively, are aligned with one another with knife blade 261 of knife assembly 260 disposed within jaw member 110 in the initial position, as discussed above. Next, pivot pin 150 is inserted through the aligned apertures.

More specifically, pivot pin 150 is first inserted through aperture 19b of shaft 12b. Next, pivot pin 150 is inserted through proximal aperture 263 of knife blade 261 such that the complementary mechanical keying features thereof engage one another. Pivot pin 150 is thereafter advanced through aperture 19a of shaft 12a. Finally, actuator arms 262 are positioned about pivot pin 150 on opposite sides thereof such that actuator arms 262 and pivot pin 150 are engaged in a mechanically-keyed relation relative to one another, as discussed above.

The different mechanical keying features of pivot pin 150 corresponding to knife blade 261 and actuator arms 262 are positioned relative to one another such that, upon assembly of forceps 10, knife blade 261 is initially disposed in the initial position, and such that actuator arms 262 are initially disposed in the un-actuated position, both under the bias of leaf spring 281 (which is disposed in the at-rest, or arched position). Visual markings or other indicia (not shown) may be provided to ensure the proper orientation and/or position of knife blade 261 and actuator arms 262 relative to pivot pin 150 and relative to each other such that this initial position is achieved upon assembly of forceps 10. Alternatively, or additionally, the mechanical keying features of actuator arms 262, knife blade 261, and/or pivot pin 150 may be configured such that pivot pin 150 may only be engaged with knife blade 261 and/or actuator arms 262 in the proper initial orientation and position, thereby helping to ensure proper assembly of forceps 10.

With reference to FIGS. 5-6, the assembly of disposable component 210 of jaw member 110 will be described. As discussed above, disposable component 210 generally includes insulative jaw housing 211, insulator 215, and electrically-conductive tissue sealing plate 219. First, as best shown in FIG. 5, tissue sealing plate 219 is positioned on insulator 215. More particularly, tissue sealing plate 219 is positioned on top of insulator 215 longitudinally between proximal base 217 of insulator 215 and distal lip 218 of insulator 215 and such that lateral wings 232 of tissue sealing plate 219 surround the longitudinal sides of insulator 215. As such, tissue sealing plate 219 and insulator 215 are retained in fixed longitudinal position relative to one another via proximal base 217 and distal lip 218 and are retained in fixed lateral position relative to one another via lateral wings 232 of tissue sealing plate 219.

With tissue sealing plate 219 disposed about insulator 215, as described above, tissue sealing plate 219 and insulator 215 are slidably engaged within jaw housing 211. More particularly, tissue sealing plate 219 and insulator 215 are slid distally into engagement with track 238 defined within jaw housing 211 from the proximal end of jaw housing 211 to the distal end of jaw housing 211 until tissue sealing plate 219 and insulator 215 are substantially fully disposed within jaw housing 211. Upon insertion of tissue sealing plate 219 and insulator 215, distal lip 218 of insulator 215 may be configured to engage an interior surface of track 238, while proximal base 217, as mentioned above, may be configured to snap-fittingly engage jaw housing 211. Further, in this configuration, tissue sealing plate 219 is inhibited from being lifted, or disengaged from jaw housing 211 via the engagement of lateral wings 232 within track 238 of jaw housing 211. In other words, jaw housing 211 secures insulator 215 and tissue sealing plate 219 therein. Additionally, or alternatively, as mentioned above, insulator 215 may be formed from a resiliently compressible material that is compressed, e.g., from an initial state to a compressed state, in order to allow insulator 215 and tissue sealing plate 219 to be slidably inserted through track 238 of jaw housing 211. Accordingly, once insulator 215 and tissue sealing plate 219 are disposed within jaw housing 211, insulator 215, tissue sealing plate 219, and jaw housing 211 are frictionally secured to one another under the bias of insulator 215, e.g., as insulator 215 attempts to resiliently returned to the initial, non-compressed state.

Referring now to FIGS. 7-8, disposable component 220 of jaw member 120 is assembled similarly to disposable component 210 of jaw member 110. More particularly, tissue sealing plate 229 is first positioned on top of insulator 225 between proximal base 227 and distal lip 228 of insulator 225 and such that lateral wings 236 of tissue sealing plate 229 surround the longitudinal sides of insulator 225. Next, tissue sealing plate 229 and insulator 225 are slid distally into engagement with track 239 defined within jaw housing 221 until tissue sealing plate 229 and insulator 225 are disposed within jaw housing 221. Once positioned within jaw housing 221, distal lip 228 of insulator 225 may be configured to engage an interior surface of track 239 and/or proximal base 227 of insulator 225 may be configured to snap-fittingly engage jaw housing 221, while lateral wings 236 of tissue sealing plate 229 are engaged within track 239 of jaw housing 221. Additionally, or alternatively, as mentioned above, insulator 225 may be formed from a resiliently compressible material to further secure the components of disposable component 220 to one another.

As can be appreciated, the above-described configuration of disposable components 210, 220 of jaw members 110, 120, respectively, obviates the need to overmold, machine, or otherwise form the components of jaw members 110, 120 to one another, thus allowing an end user to assemble and disassemble jaw members 110, 120 without the need for specialized equipment.

With disposable components 210, 220 of jaw members 110, 120 fully assembled, as described above, disposable components 210, 220 may be snap-fittingly engaged to their respective jaw frames 112, 122, to complete the assembly of forceps 10. Alternatively, either (or both) of the jaw housings 211, 221 may be configured for slidable positioning about the respective insulator 215, 225 and tissue sealing plate 219, 229, as well as the respective jaw frame 112, 122, to secure the respective disposable component 210, 220 to the corresponding jaw frame 112, 122 (as opposed to the snap-fitting arrangement discussed above). In other words, the insulators 215, 225 and tissue seal plates 219, 229 may first be positioned on the jaw frames 112, 122, respectively, with the respective jaw housing 211, 221 subsequently slide-fit thereabout to secure the respective insulators 215, 225, tissue sealing plates 219, 229, and jaw frames 112, 122 of each jaw member 110, 120 to one another.

Turning now to FIGS. 12-14B, the use and operation of forceps 10 will be described. Initially, the reusable portion(s) of forceps 10, e.g., shafts 12a, 12b, are sterilized and/or otherwise prepared for use (or reuse). Next, forceps 10 is assembled as described above. At this point (or prior to), an electrosurgical energy source (not shown) may be coupled to tissue sealing plate 219 and/or tissue sealing plate 229 of jaw members 110, 120, respectively, e.g., via an electrosurgical cable (not shown) coupled at a first end to the energy source (not shown) and at a second end to lateral flange 231 and/or lateral flange 233 of tissue sealing plates 219, 229, respectively (see FIGS. 5-8). However, the electrical connection(s) may alternatively be configured to run through either of shafts 12a, 12b, or may otherwise be configured to supply energy to tissue sealing plates 219, 229 via any other suitable mechanism. With forceps 10 fully assembled (and with the electrical connections intact), forceps 10 is ready for use.

Referring to FIG. 12, shafts 12a and 12b are moved to the spaced-apart position such that jaw members 110, 120, disposed at distal ends 14a, 14b, of shafts 12a and 12b, respectively, are moved to the open position. At this point, leaf spring 281 is disposed in the at-rest position, cam pin 284 is disposed at the proximal ends 15a, 267 of cam slots 13a, 266, respectively, actuator arms 262 are disposed in the un-actuated position, and knife blade 261 is disposed in the initial position. With jaw members 110, 120 disposed in the open position, as shown in FIG. 12, forceps 10 may be manipulated into position such that tissue to be grasped, sealed and/or divided is disposed between jaw members 110, 120.

Once tissue is positioned as desired, shafts 12a and 12b may be moved toward one another, e.g., to the first approximated position, to pivot jaw members 110, 120 about pivot pin 150 toward the closed position to grasp tissue between tissue sealing plates 219, 229 of disposable components 210, 220, of jaw members 110, 120 respectively, as shown in FIG. 13A. Shafts 12a and 12b may be approximated relative to one another to selectively engage ratchet 30 such that the user may control the closure force applied to tissue grasped between jaw members 110, 120. Next, the user may selectively apply electrosurgical energy to electrically-conductive tissue sealing plates 219 and 229 of jaw members 110 and 120, respectively, to seal tissue grasped between jaw members 110, 120.

Referring now to FIGS. 13A-13B, although shafts 12a, 12b have been moved to the first approximated position to move jaw members 110, 120 to the closed position to grasp tissue between sealing plates 219, 229, respectively, thereof, at this point, leaf spring 281 remains disposed in the at-rest position, cam pin 284 remains disposed at the proximal ends 15a, 267 of cam slots 13a, 266, actuator arms 262 remain disposed in the un-actuated position, and knife blade 261 remains disposed in the initial position.

When it is desired to cut tissue grasped between jaw members 110, 120, shafts 12a, 12b are moved closer to one another, e.g., toward the second approximated position. As shafts 12a, 12b are moved toward the second approximated position, the ratchet 30 is moved to an over-extended position wherein the teeth of ratchet 30 no longer engage one another, e.g., such that shaft members 12a, 12b are thereafter continuously movable to the second approximated position. Eventually, upon translation of shafts 12a, 12b toward the second approximated position, shaft 12b contacts the arch-shaped leaf spring 281. Upon further approximation of shafts 12a, 12b, shaft 12b urges leaf spring 281 from the arch-shaped configuration to a relatively linear-shaped configuration. In other words, shaft 12b urges the apex of arch-shaped leaf spring 281 toward shaft 12a such that the distal end 282 of leaf spring 281 and, thus, cam pin 284 which is coupled thereto, are urged distally.

As cam pin 284 is urged distally through cam slots 13a, 266, of shaft 12a and actuator arms 262, respectively, actuator arms 262 are rotated about pivot pin 150 relative to shaft 12a and end effector assembly 100 from the un-actuated position (FIG. 13A) to the actuated position (FIG. 14A), due to the angled, or mis-aligned positioning of cam slots 266 of actuator arms 262 relative to cam slots 13a of shaft 12a. As shown in FIGS. 14A-14B, as actuator arms 262 are rotated about pivot pin 150 to the actuated position, pivot pin 150 is rotated due to the mechanical-keying engagement therebetween and, in turn, knife blade 261 is rotated due to the mechanical-keying engagement between knife blade 261 and pivot pin 150. More specifically, as best shown in FIG. 14B, knife blade 261 is rotated from the initial position within jaw member 110 to the extended position, wherein knife blade 261 extends between jaw members 110, 120, e.g., through blade slot 116 defined within jaw frame 112, elongated aperture 214 defined within jaw housing 211, blade channel 216 defined within insulator 215, and blade channel 235 of tissue sealing plate 219, to cut tissue grasped therebetween. Ultimately, once shafts 12a, 12b reach the second approximated position, knife blade 261 may be configured to extend completely through tissue and into blade channel 237 defined within tissue sealing plate 229 of jaw member 120.

Once tissue has been grasped, sealed and/or divided, jaw members 110, 120 may be returned to the open position, e.g., via moving shafts 12a, 12b back to the spaced-apart position, to release the sealed and divided tissue. As shafts 12a, 12b are returned to the spaced-apart position, shaft 12b is moved apart from leaf spring 281, allowing leaf spring 281 to return to its at-rest position. As leaf spring 281 is returned to its at-rest position, cam pin 284 is translated proximally such that actuator arms 262 are rotated back to the un-actuated position and such that knife blade 261 is returned to the initial position. Once jaw members 110, 120 have been moved to the open position to release tissue, forceps 10 may be removed from the surgical site.

At the completion of the surgical procedure, disposable components 210, 220 may be removed from jaw frames 112, 122 of jaw members 110, 120, respectively, and discarded. Additionally, forceps 10 may be further disassembled, e.g., knife assembly 260 may be removed and discarded, such that the remaining components of forceps 10 may be sterilized for reuse. Thereafter, forceps 10 may be reassembled with new disposable components 210, 220 and a new knife assembly 260 for subsequent use.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly including:
first and second jaw members; and
a pivot pin coupling the first and second jaw members to one another, wherein the first and second jaw members are movable relative to one another about the pivot pin between an open position and a closed position; and
a knife assembly, including:
a knife blade mechanically keyed to the pivot pin and movable between an initial position wherein the knife blade is disposed within one of the first and second jaw members, and an extended position wherein the knife blade extends at least partially between the first and second jaw members; and
an actuator mechanically keyed to the pivot pin and extending therefrom, the actuator selectively actuatable to rotate the pivot pin relative to the first and second jaw members to move the knife blade from the initial position to the extended position.

2. The forceps according to claim 1, wherein at least one of the first and second jaw members includes a seal plate adapted to connect to a source of energy.

3. The forceps according to claim 1, wherein at least one of the first and second jaw members includes a longitudinally-extending blade channel defined at least partially therethrough, the blade channel configured to permit passage of the knife blade therethrough upon movement of the knife blade from the initial position to the extended position.

4. The forceps according to claim 1, wherein at least one of the first and second jaw members includes:
a jaw frame; and
a jaw housing releasably engagable with the jaw frame.

5. The forceps according to claim 4, wherein the jaw housing includes at least one engagement feature configured to releasably engage a complementary engagement feature defined within the jaw frame.

6. The forceps according to claim 1, further including at least one shaft member coupled to the end effector assembly, the at least one shaft member operable to move the first and second jaw members about the pivot pin between the open position and the closed position.

7. The forceps according to claim 1, wherein a shaft member is coupled to each of the first and second jaw members, the shaft members movable relative to one another between a spaced-apart position and an approximated position for moving the jaw members about the pivot pin between the open position and the closed position.

8. An end effector assembly of a surgical instrument, comprising:
first and second jaw members;
a pivot pin coupling the first and second jaw members to one another, wherein the first and second jaw members are rotatable relative to one another about the pivot pin between an open position and a closed position; and
a knife blade coupled to the pivot pin such that rotation of the pivot pin relative to the first and second jaw members rotates the knife blade relative to the first and second jaw members between an initial position, wherein the knife blade is disposed within one of the first and second jaw members, and an extended position, wherein the knife blade extends at least partially between the first and second jaw members.

9. The end effector assembly according to claim 8, further including an actuator coupled to the pivot pin, the actuator selectively actuatable to rotate the pivot pin relative to the first and second jaw members to move the knife blade from the initial position to the extended position.

10. The end effector assembly according to claim 8, wherein at least one of the first and second jaw members includes a seal plate adapted to connect to a source of energy.

11. The end effector assembly according to claim 8, wherein at least one of the first and second jaw members includes a longitudinally-extending blade channel defined at least partially therethrough, the blade channel configured to permit passage of the knife blade therethrough upon movement of the knife blade from the initial position to the extended position.

* * * * *